(12) United States Patent  
Sugimoto

(10) Patent No.: US 8,348,836 B2  
(45) Date of Patent: Jan. 8, 2013

(54) SCANNING ENDOSCOPE, SCANNING ENDOSCOPE PROCESSOR, AND SCANNING ENDOSCOPE APPARATUS

(75) Inventor: Hideo Sugimoto, Tokyo (JP)

(73) Assignee: Hoya Corporation, Tokyo (JP)

(*) Notice: Subject to any disclaimer, the term of this patent is extended or adjusted under 35 U.S.C. 154(b) by 529 days.

(21) Appl. No.: 12/619,915

(22) Filed: Nov. 17, 2009

(65) Prior Publication Data

US 2010/0125167 A1    May 20, 2010

(30) Foreign Application Priority Data

Nov. 19, 2008 (JP) ................................ 2008-296159

(51) Int. Cl.  
 *A61B 1/06* (2006.01)
(52) U.S. Cl. .......................................... 600/160; 348/65
(58) Field of Classification Search .................. 600/160; 348/65; 359/196  
See application file for complete search history.

(56) References Cited

U.S. PATENT DOCUMENTS

| | | | |
|---|---|---|---|
| 6,294,775 B1 | 9/2001 | Seibel et al. | |
| 7,129,472 B1 | 10/2006 | Okawa et al. | |
| 7,194,153 B1* | 3/2007 | Yajima et al. | 385/18 |
| 7,608,842 B2* | 10/2009 | Johnston | 250/492.1 |
| 7,753,842 B2* | 7/2010 | Glukhovsky et al. | 600/130 |
| 7,835,074 B2* | 11/2010 | Jacobsen et al. | 359/367 |
| 7,914,447 B2* | 3/2011 | Kanai | 600/160 |
| 2007/0035797 A1 | 2/2007 | Kanai | |
| 2007/0276184 A1* | 11/2007 | Okawa | 600/117 |
| 2008/0138091 A1* | 6/2008 | Shimoguchi | 398/200 |
| 2009/0201495 A1* | 8/2009 | Hiramoto et al. | 356/243.4 |
| 2010/0010302 A1* | 1/2010 | Hadani | 600/109 |
| 2010/0053312 A1* | 3/2010 | Watanabe et al. | 348/65 |

FOREIGN PATENT DOCUMENTS

| | | |
|---|---|---|
| JP | 2001-174744 | 6/2001 |
| JP | 3943927 | 4/2007 |
| JP | 2008-504557 | 2/2008 |
| WO | 2006/004743 | 1/2006 |

OTHER PUBLICATIONS

Machine translation of JP2005-091936, Hieta et al. "Variable Optical Attenuatior and Method".*  
U.S. Appl. No. 12/619,934 to Sugimoto, which was filed Nov. 17, 2009.

* cited by examiner

*Primary Examiner* — Clayton E LaBalle  
*Assistant Examiner* — Linda B Smith  
(74) *Attorney, Agent, or Firm* — Greenblum & Bernstein, P.L.C.

(57) ABSTRACT

A scanning endoscope, comprising a first transmitter, an actuator, and a mirror, is provided. The first transmitter emits a beam of radiant light from an emission end. The actuator moves the emission end in a direction perpendicular to an emission direction. The mirror is arranged from the emission end in the emission direction when the emission end is on a predetermined standard point. The mirror comprises a reflection surface around a first straight line. The distance between a first position on the first straight line to any second position on the reflection surface increases as the first position is moved in the first direction. The reflection surface reflects the radiant light emitted from the first transmitter toward the observation area around the first straight line.

4 Claims, 19 Drawing Sheets

FIRST DIRECTION

SCANNING ENDOSCOPE, SCANNING ENDOSCOPE PROCESSOR, AND SCANNING ENDOSCOPE APPARATUS

BACKGROUND OF THE INVENTION

1. Field of the Invention

The present invention relates to a scanning endoscope that photographs and/or films an optical image of a subject that is around an insertion tube of the scanning endoscope.

2. Description of the Related Art

Japanese Patent No. 3943927 discloses a scanning endoscope which photographs and/or films an optical image of an observation area by scanning the observation area with light shined on a minute point in the area and successively capturing reflected light at the illuminated points. In a general scanning endoscope, light for illumination is transmitted through an optical fiber from a stationary incident end to a movable emission end and a scanning operation is carried out by successively moving the emission end of the optical fiber.

A general scanning endoscope is designed so that a field of vision of the scanning endoscope is in front of a distal end of an insertion tube of the scanning endoscope. However, it is difficult to observe certain types of subjects using such a scanning endoscope. This is because it is difficult to adjust the position of the insertion tube in a thin lumen, such as a bronchial periphery, so that the distal end of the insertion tube faces the inner surface of the thin lumen. Accordingly, the inner surface of a thin lumen is photographed and/or filmed at a large angle of incidence with respect to the inner surface to be photographed and/or filmed. However, it is difficult to recognize the status of the inner surface by the image of the inner surface photographed and/or filmed from such a large angle of incidence.

SUMMARY OF THE INVENTION

Therefore, an object of the present invention is to provide a scanning endoscope that can photograph and/or film an optical image of the subject around an insertion tube with a direct front view.

According to the present invention, a scanning endoscope, comprising a first transmitter, an actuator, and a mirror, is provided. The first transmitter emits a beam of radiant light from an emission end. The beam of the radiant light is shined on an observation area. The actuator moves the emission end in a direction perpendicular to an emission direction. The beam of the radiant light is emitted from the emission end of the first transmitter in the emission direction. The mirror is arranged from the emission end in the emission direction when the emission end is on a predetermined standard point. The mirror comprises a reflection surface around a first straight line. The first straight line is parallel to a first direction and including the standard point. The first direction is the emission direction of the radiant light when the emission end is on the standard point. The distance between a first position on the first straight line to any second position on the reflection surface increases as the first position is moved in the first direction. The reflection surface reflects the radiant light emitted from the first transmitter toward the observation area around the first straight line. A line connecting the first and second positions is perpendicular to the first straight line.

According to the present invention, a scanning endoscope processor, comprising a light source, a light receiver, an image processor, and a first controller, is provided. The light source supplies the radiant light to the first transmitter of the scanning endoscope. The light receiver receives and detects an amount of the reflected light or the fluorescence at the observation area illuminated with the radiant light. The image processor produces an image corresponding to the observation area on the basis of the amount of the reflected light or the fluorescence detected by the light receiver. The first controller suspends the production of an image at the image processor when the emission end is within the first area. The first controller orders the image processor to produce the image when the emission end is outside of the first area.

According to the present invention, a scanning endoscope apparatus, comprising the scanning endoscope and the scanning endoscope processor, is provided.

BRIEF DESCRIPTION OF THE DRAWINGS

The objects and advantages of the present invention will be better understood from the following description, with reference to the accompanying drawings in which.

DESCRIPTION OF THE PREFERRED EMBODIMENTS

Figure 1:
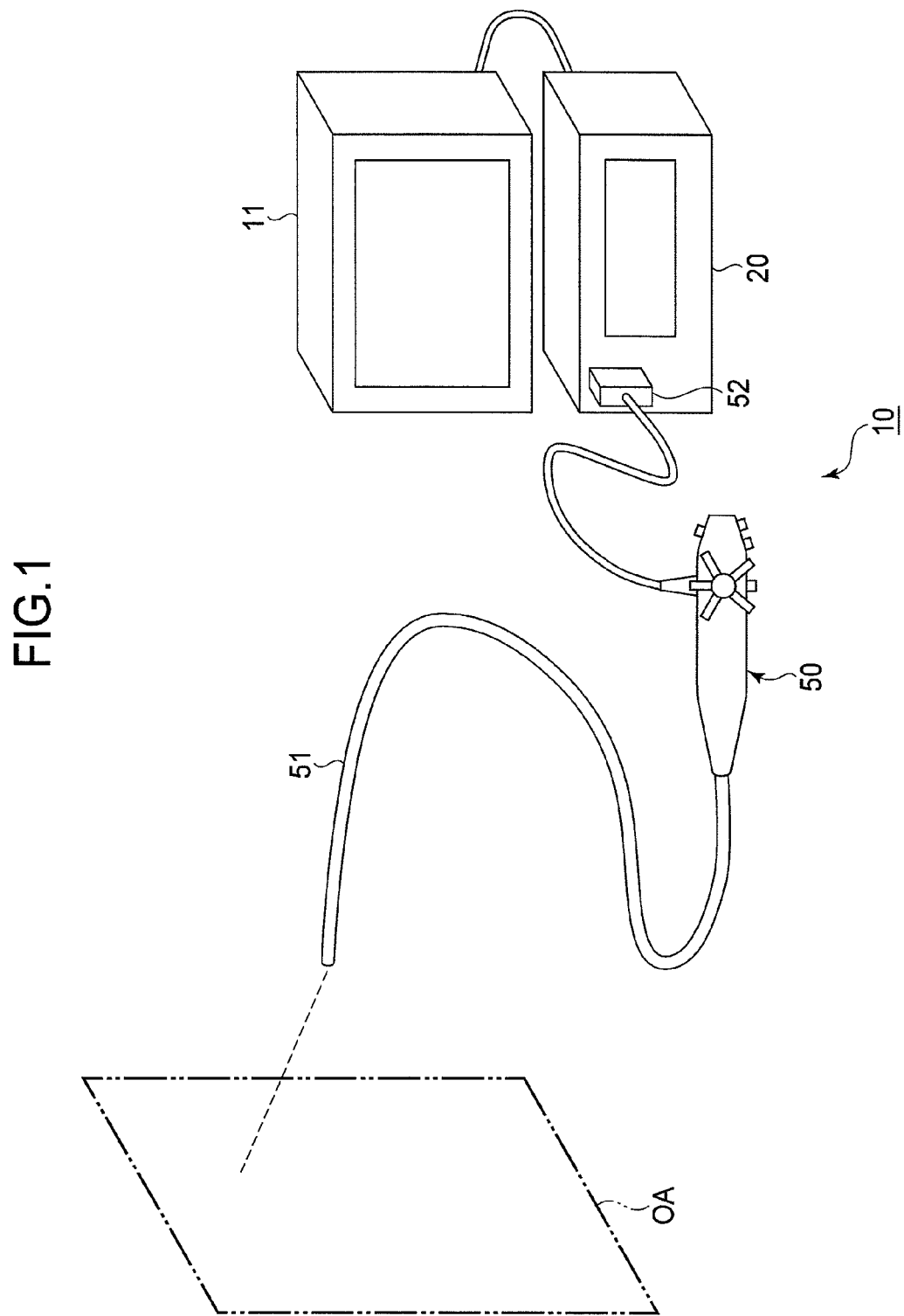
FIG. 1 is a schematic illustration of a scanning endoscope apparatus comprising a scanning endoscope and a scanning endoscope processor of an embodiment of the present invention.

The present invention is described below with reference to the embodiment shown in the drawings.

In FIG. 1, the scanning endoscope apparatus 10 comprises a scanning endoscope processor 20, a scanning endoscope 50, and a monitor 11. The scanning endoscope processor 20 is connected to the scanning endoscope 50 and the monitor 11.

Hereinafter, an emission end of an illumination fiber (not depicted in FIG. 1) and incident ends of image fibers (not depicted in FIG. 1) are ends mounted in the distal end of the insertion tube 51 of the scanning endoscope 50. In addition, an incident end of the illumination fiber and emission ends of the image fibers are ends mounted in a connector 52 that connects to the scanning endoscope processor 20.

The scanning endoscope processor 20 provides light that is shined on an observation area (see "OA" in FIG. 1). The light emitted from the scanning endoscope processor 20 is transmitted to the distal end of the insertion tube 51 through the illumination fiber (first transmitter), and is shined towards one point in the observation area. Light reflected from the illuminated point is transmitted from the distal end of the insertion tube 51 to the scanning endoscope processor 20.

The direction of the emission end of the illumination fiber is changed by a fiber actuator (not depicted in FIG. 1). By changing the direction, the observation area is scanned with the light emitted from the illumination fiber. The fiber actuator is controlled by the scanning endoscope processor 20.

The scanning endoscope processor 20 receives reflected light which is scattered at the illuminated point, and generates a pixel signal according to the amount of received light. One frame of an image signal is generated by generating pixel signals corresponding to the illuminated points entirely dispersed in the observation area. The generated image signal is transmitted to the monitor 11, where an image corresponding to the received image signal is displayed.

Figure 2:
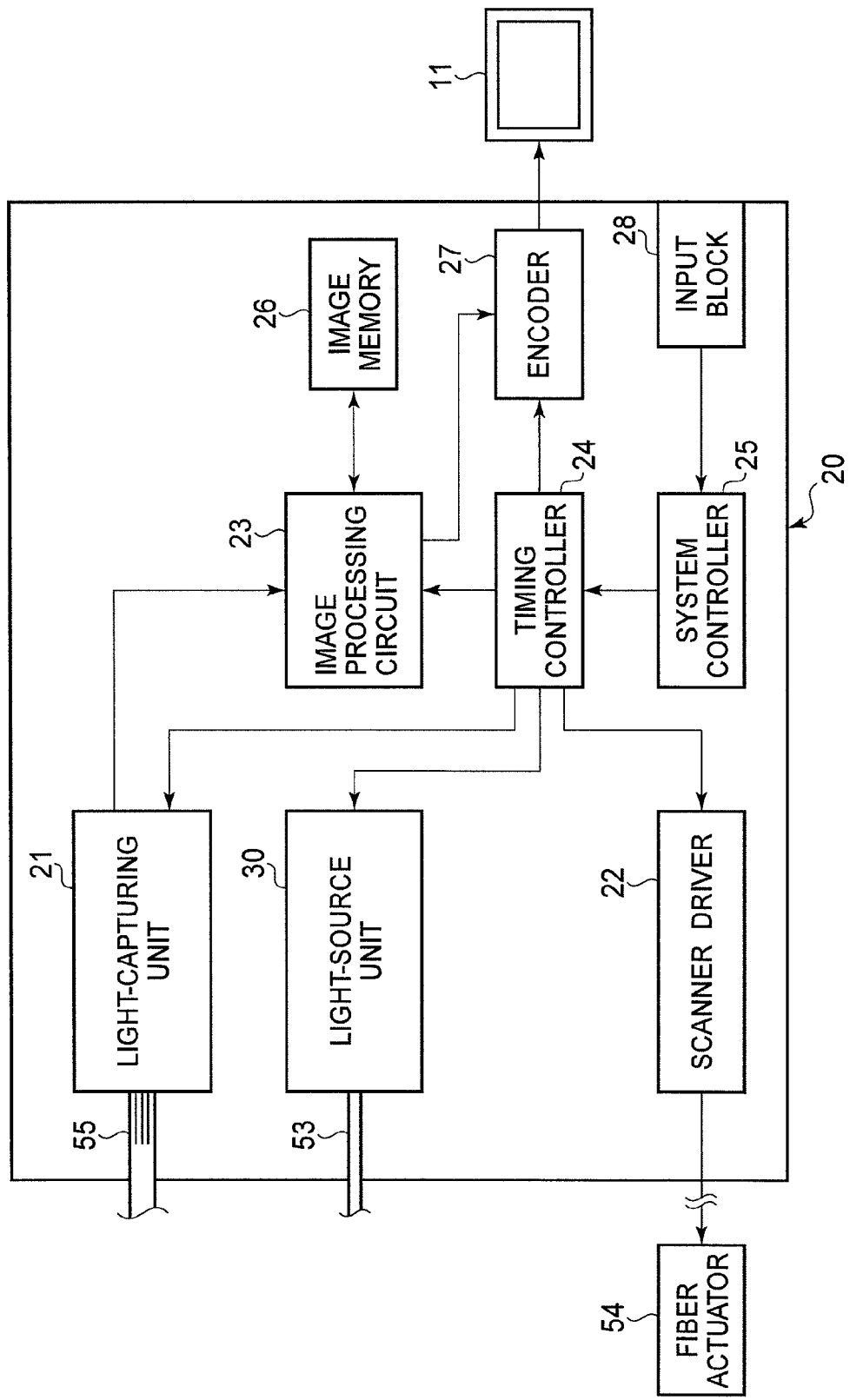
FIG. 2 is a block diagram schematically showing the internal structure of the scanning endoscope processor.

As shown in FIG. 2, the scanning endoscope processor 20 comprises a light-source unit 30, a light-capturing unit 21, a scanner driver 22, an image processing circuit 23, a timing controller 24, a system controller 25 (first to third controllers), and other components.

The light-source unit 30 comprises red, green, and blue lasers (not depicted), which emits red, green, and blue laser beams, respectively. The red, green, and blue laser beams are mixed into a white laser beam, which is emitted from the light-source unit 30.

The light-source unit 30 provides the illumination fiber 53 with a white laser beam that is emitted from the light-source unit 30. The scanning driver 22 controls the fiber actuator 54 to move the emission end of the illumination fiber 53 along a predetermined course. As described above, the light transmitted to the emission end of the illumination fiber 53 is emitted in the axis direction of the illumination fiber 53 at the emission end.

The light reflected from the observation area is transmitted to the scanning endoscope processor 20 by the image fibers 55 (second transmitter) that constitute the scanning endoscope 50. The transmitted light is made incident on the light-capturing unit 21.

The light-capturing unit 21 generates a pixel signal according the amount of the reflected light. The pixel signal is transmitted to the image processing circuit 23, which stores the received pixel signal in the image memory 26. Once pixel signals corresponding to the illuminated points dispersed throughout the observation area have been stored, the image processing circuit 23 carries out predetermined image processing on the pixel signals, and then one frame of the image signal is transmitted to the monitor 11 via the encoder 27.

By connecting the scanning endoscope 50 to the scanning endoscope processor 20, optical connections are made between the light-source unit 30 and the illumination fiber 53 mounted in the scanning endoscope 50, and between the light-capturing unit 21 and the image fibers 55. In addition, by connecting the scanning endoscope 50 to the scanning endoscope processor 20, the fiber actuator 54 mounted in the scanning endoscope 50 is electrically connected with the scanning driver 22.

The timing for carrying out operations of the light-source unit 30, the light-capturing unit 21, the image processing circuit 23, the scanning driver 22, and the encoder 27 is controlled by the timing controller 24. In addition, the timing controller 24 and other components of the endoscope apparatus 10 are controlled by the system controller 25. A user can input some commands to the input block 28, which comprises a front panel (not depicted) and other mechanisms.

Figure 3:
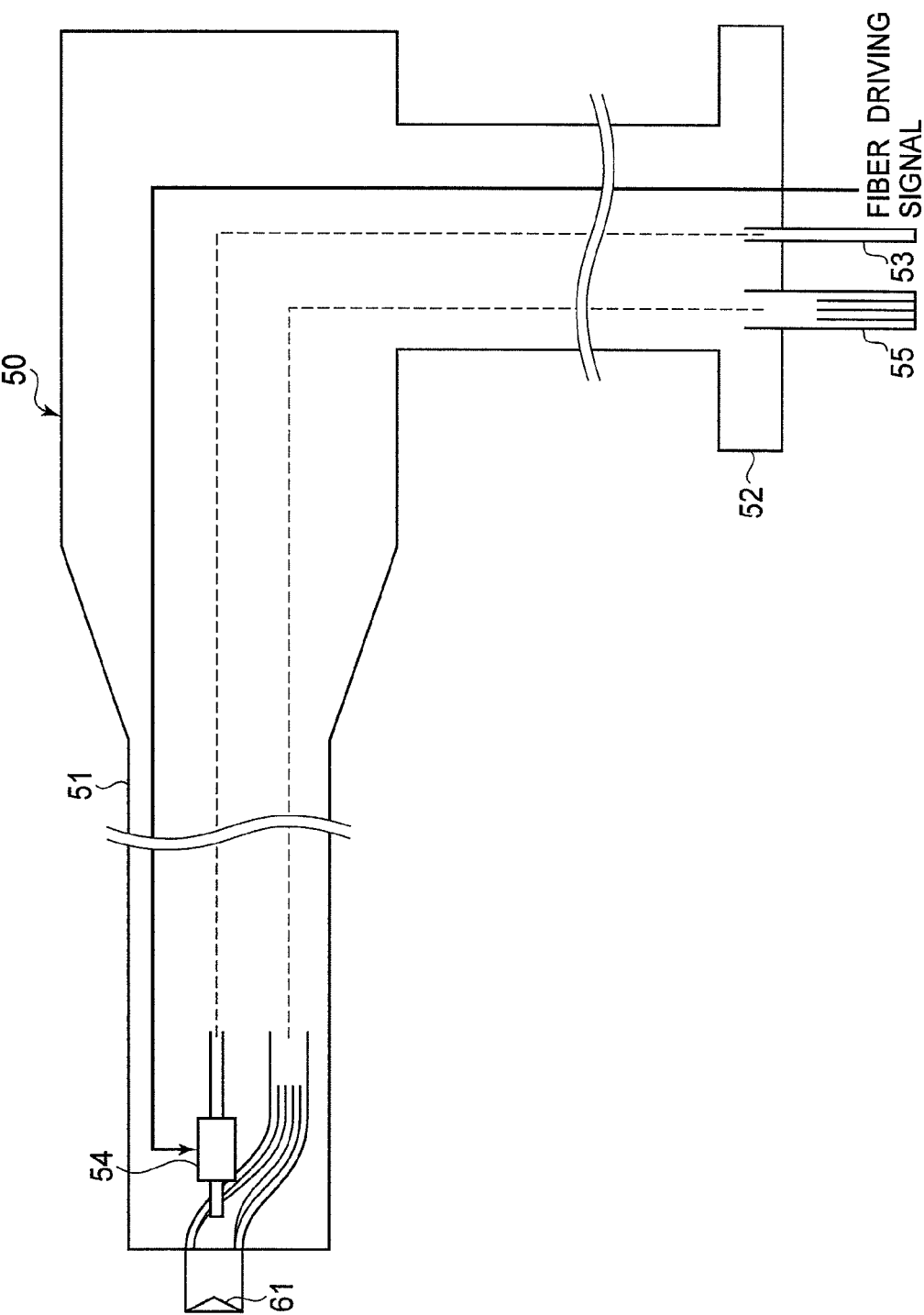
FIG. 3 is a block diagram schematically showing the internal structure of the scanning endoscope.

Next, the structure of the scanning endoscope 50 is explained. As shown in FIG. 3, the scanning endoscope 50 comprises the illumination fiber 53, the fiber actuator 54, the image fibers 55, a mirror 61, and other components.

The illumination fiber 53 and the image fibers 55 are arranged inside the scanning endoscope 50 from the connector 52 to the distal end of the insertion tube 51. As described above, the white laser beam emitted by the light-source unit 30 is incident on the incident end of the illumination fiber 53. The incident white laser beam is transmitted to the emission end of the illumination fiber 53.

Figure 4:
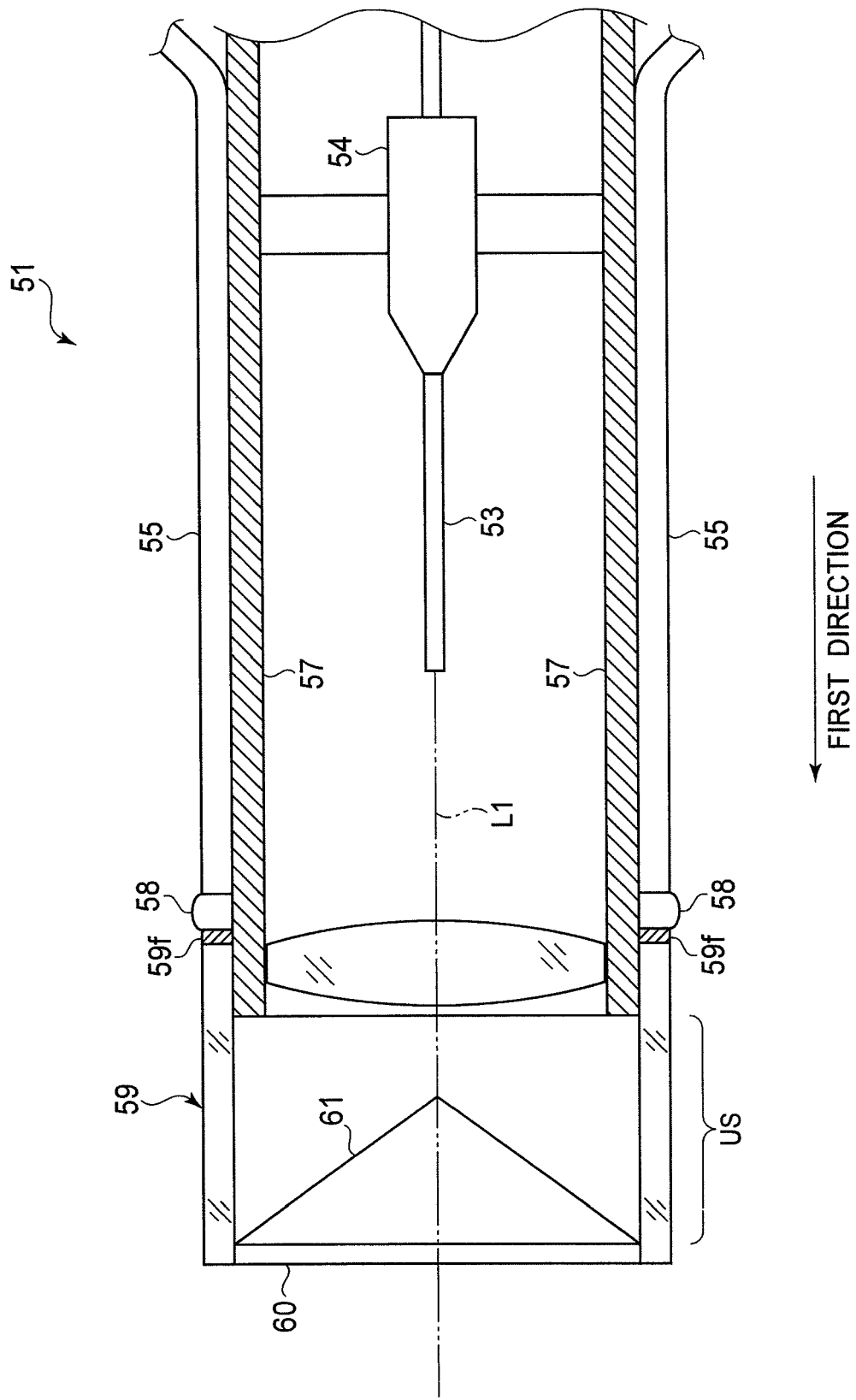
FIG. 4 is a sectional view of the emission end of the illumination fiber along the axis direction of the illumination fiber.

As shown in FIG. 4, a solid hollow tube 57 is mounted at the distal end of the insertion tube 51. The hollow tube 57 is positioned so that the axis direction of the distal end of the insertion tube 51 is parallel to a first direction that is an axis direction of the hollow tube 57.

The illumination fiber 53 is supported inside the hollow tube 57 by the fiber actuator 54. The illumination fiber 53 is positioned in the hollow tube 57 so that the axis direction of the hollow tube 57 is parallel to an axis direction of the insertion tube 51 that is not moved by the fiber actuator 54.

Figure 5:
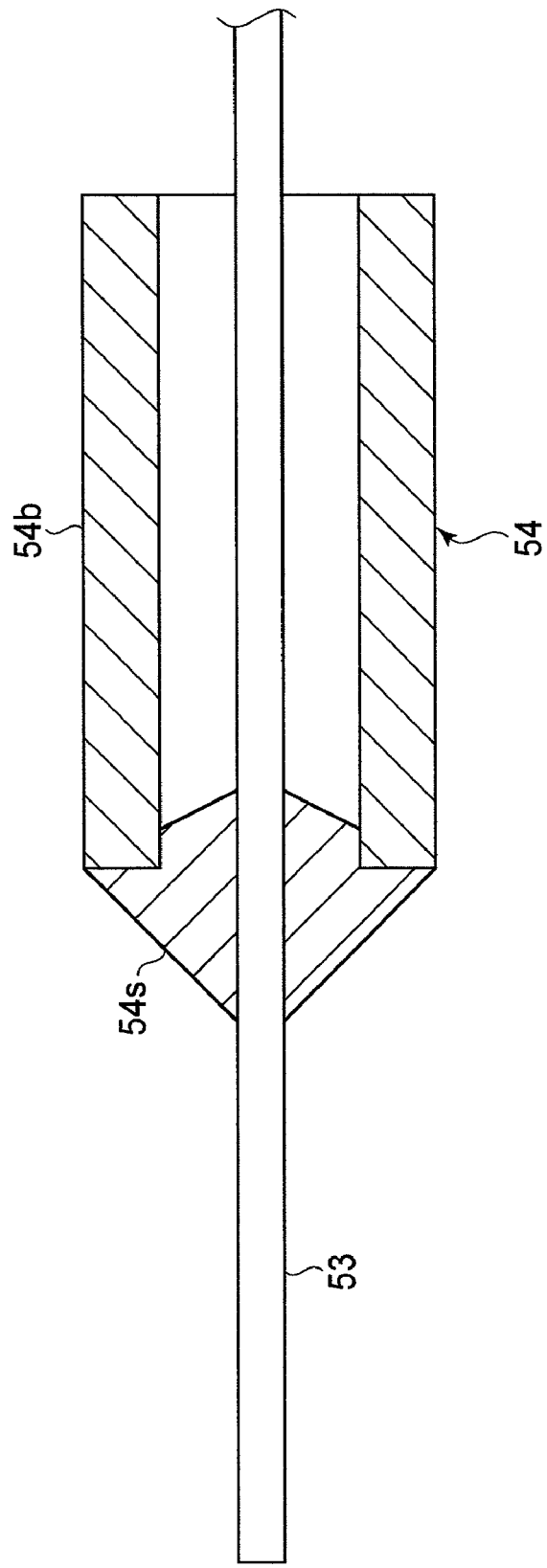
FIG. 5 is a sectional view of the fiber actuator along the axis direction of the illumination fiber, which has been provided for the purpose of illustrating the structure of the fiber actuator.

As shown in FIG. 5, the fiber actuator 54 comprises a supporting block 54s and a bending block 54b. The bending block 54b is shaped cylindrically. The illumination fiber 53 is inserted through the cylindrical bending block 54b. The illumination fiber 53 is supported at the forward end of the bending block 54b nearest the distal end of the insertion tube 51 by the supporting block 54s.

Figure 6:
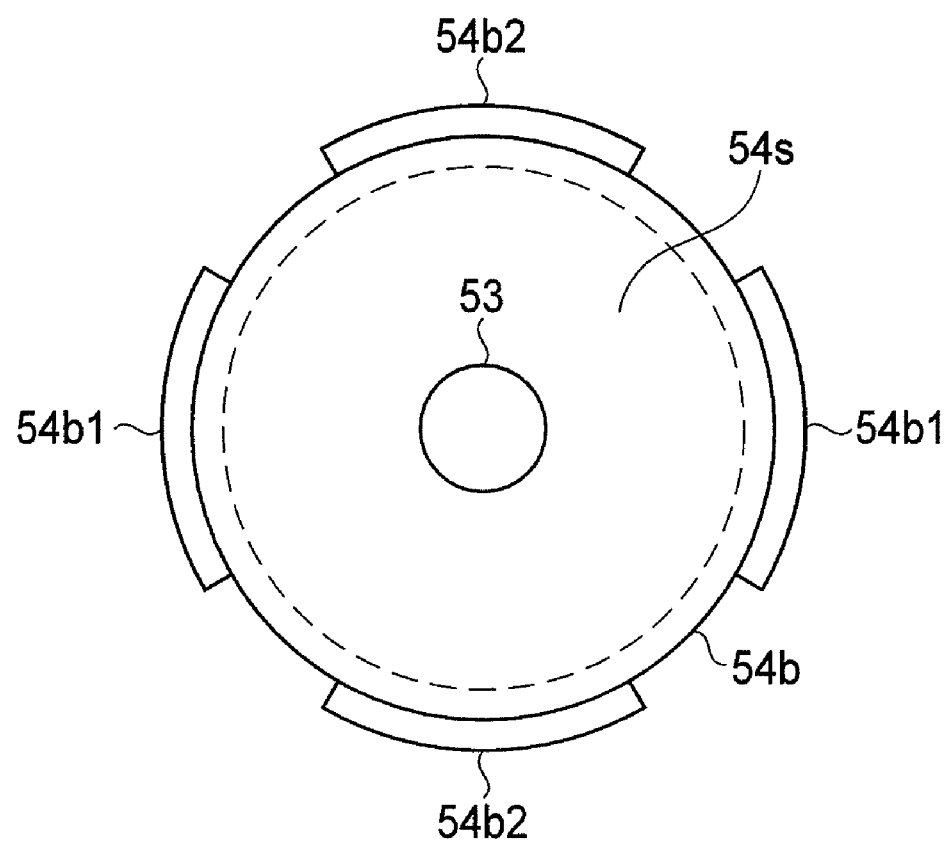
FIG. 6 is a front view of the fiber actuator as seen from the emission end of the illumination fiber.

As shown in FIG. 6, first and second bending elements 54b1 and 54b2 are fixed on the bending block 54b. The first and second bending elements 54b1 and 54b2 are pairs of two piezoelectric elements. In addition, the first and second bending elements 54b1 and 54b2 expand and contract along the axis direction of the cylindrical bending block 54b on the basis of a fiber driving signal transmitted from the scanner driver 22.

Two piezoelectric elements that constitute the first bending elements 54b1 are fixed on the outside surface of the cylindrical bending block 54b so that the axis of the cylindrical bending block 54b is between the piezoelectric elements. In addition, two piezoelectric elements that constitute the second bending elements 54*b*2 are fixed on the outside surface of the cylindrical bending block 54*b* at a location that is 90 degrees circumferentially from the first bending element 54*b*1 around the axis of the cylindrical bending block 54*b*.

Figure 7:
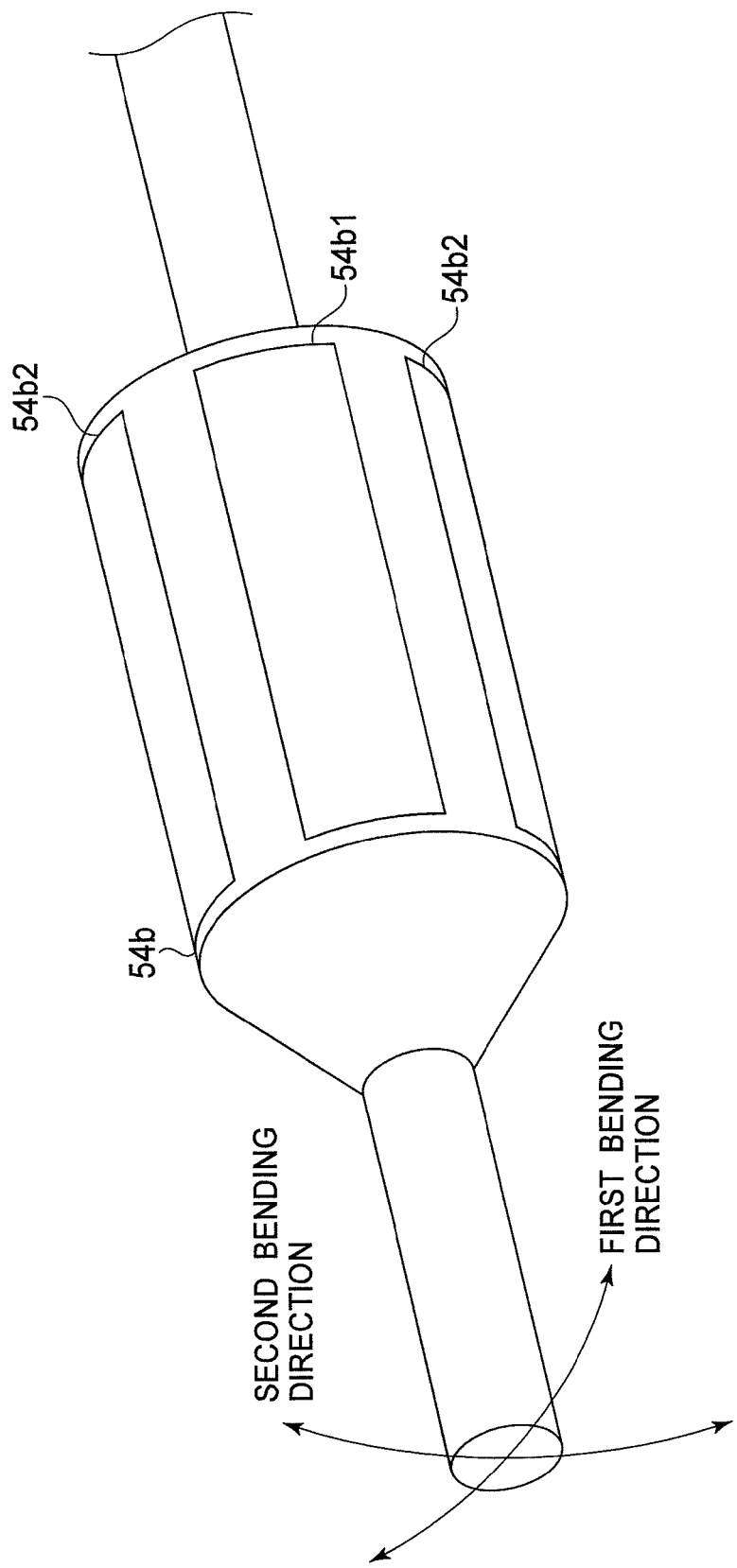
FIG. 7 is a perspective view of the fiber actuator.

As shown in FIG. 7, the bending block 54*b* bends along a first bending direction by expanding one of the piezoelectric element that constitute the first bending element 54*b*1 and contracting the other at the same time. The piezoelectric elements constituting the first bending element 54*b*1 are arranged along the first bending direction.

In addition, the bending block 54*b* bends along a second bending direction by expanding one of the piezoelectric element that constitute the second bending element 54*b*2 and contracting the other at the same time. The piezoelectric elements constituting the second bending element 54*b*2 are arranged along the second bending direction.

The side of illumination fiber 53 is pushed along the first and/or second bending directions by the bending block 54*b* via the supporting block 54*s*, and the illumination fiber 53 bends toward the first and/or second bending directions, which are perpendicular to the axis direction of the illumination fiber 53. By bending the illumination fiber 53, the emission end of the illumination fiber 53 is moved in the directions perpendicular to the axis direction of the illumination fiber 53 at the emission end.

Figure 8:
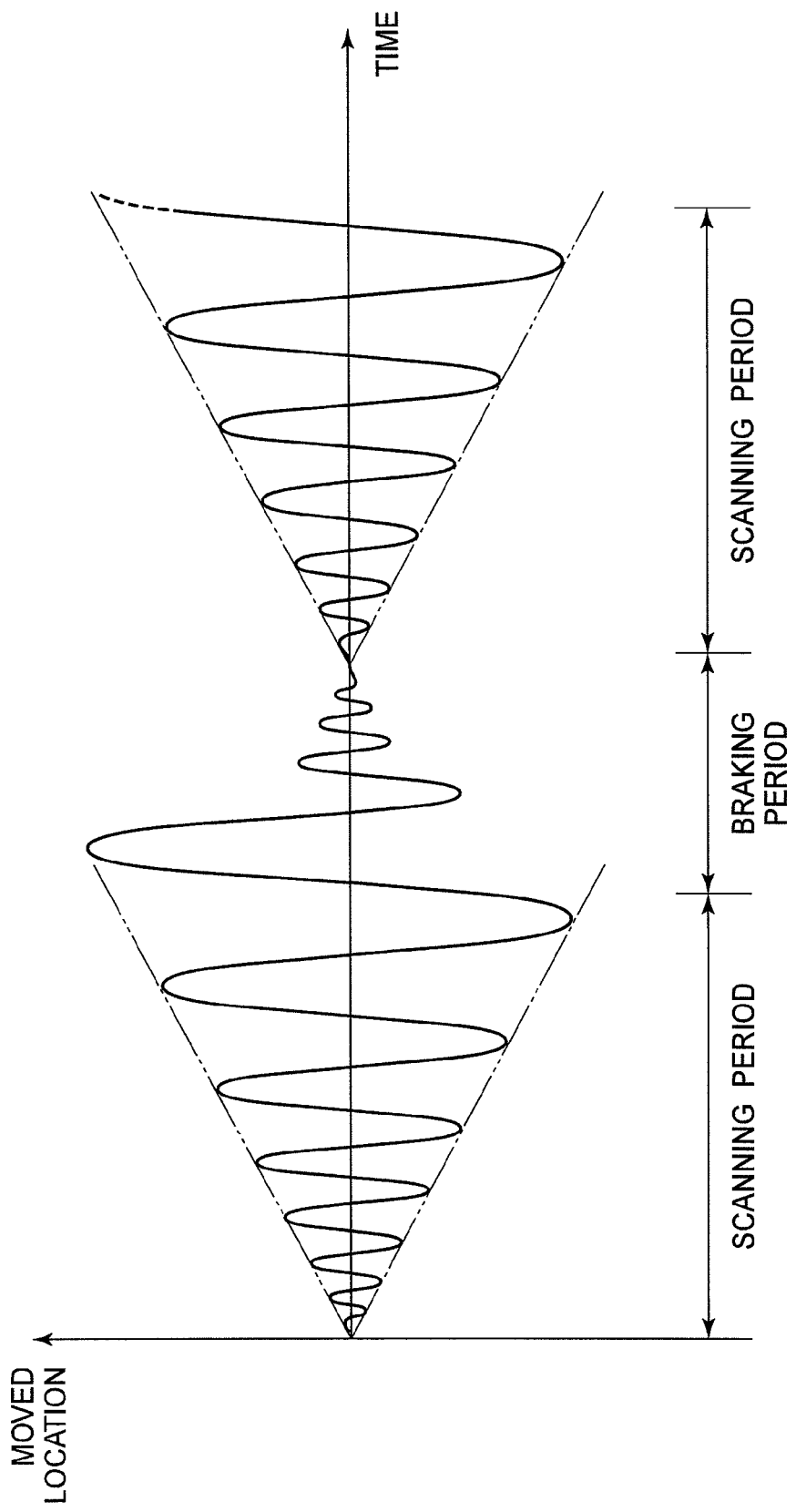
FIG. 8 is a graph illustrating the change in position of the emission end from the standard point along the first and second bending directions.

As shown in FIG. 8, the emission end of the illumination fiber 53 is moved so that the emission end vibrates along the first and second bending directions at amplitudes that are repetitively increased and decreased. The frequencies of the vibration along the first and second bending directions are adjusted to be equal. In addition, the period to increase and to decrease the amplitudes of the vibration along the first and second bending directions are synchronized. Further, phases of the vibration along the first and second bending directions are shifted by 90 degrees.

Figure 9:
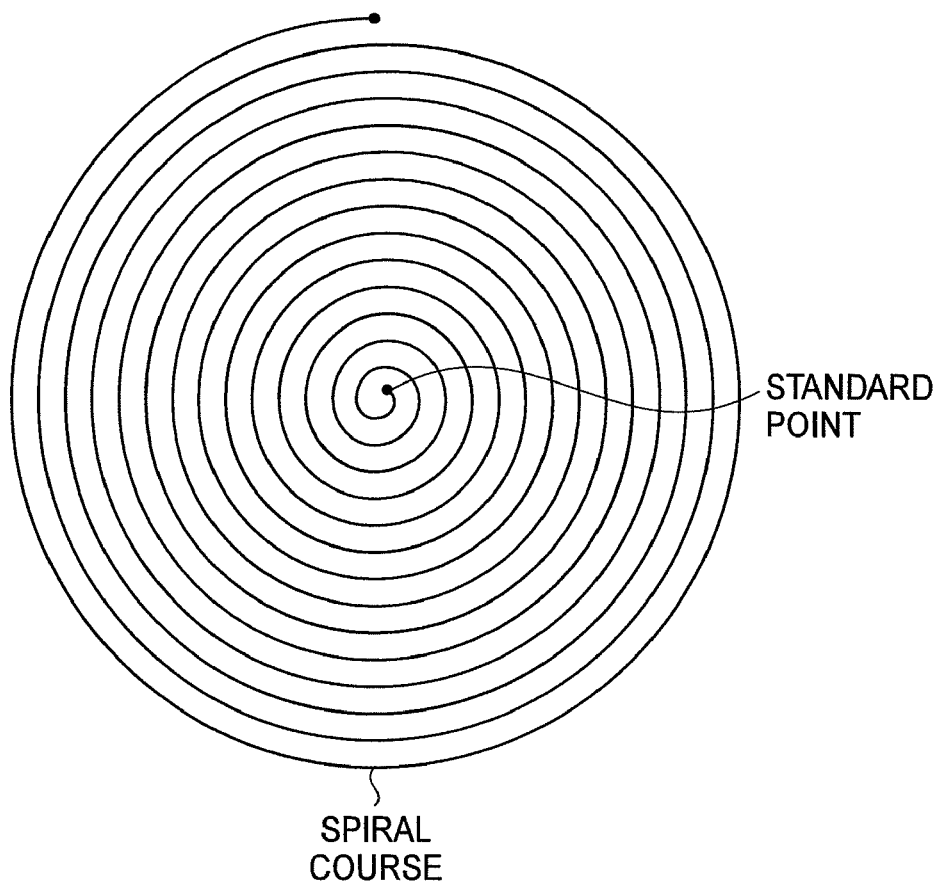
FIG. 9 illustrates a spiral course along which the emission end of the illumination fiber is moved by the fiber actuator.

By vibrating the emission end of the illumination fiber 53 along the first and second bending directions as described above, the emission end traces the spiral course shown in FIG. 9, and the observation area is scanned with the white laser beam.

The position of the emission end of the illumination fiber 53 when it is not bent is defined as a standard point. As described later, while the emission end is vibrated with increasing amplitude starting from the standard point (see "scanning period" in FIG. 8), illumination of the observation area with the white laser beam and generation of pixel signals are carried out.

In addition, when the amplitude reaches a maximum among the predetermined range, one scanning operation for producing one image terminates. After termination of a scanning operation, the emission end of the illumination fiber 53 is returned to the standard point by vibration of the emission end along the first and second bending directions at decreasing amplitudes during a braking period, as shown in FIG. 8. When the emission end is moved to the standard point, it is the beginning of a scanning operation for generating another image.

Figure 10:
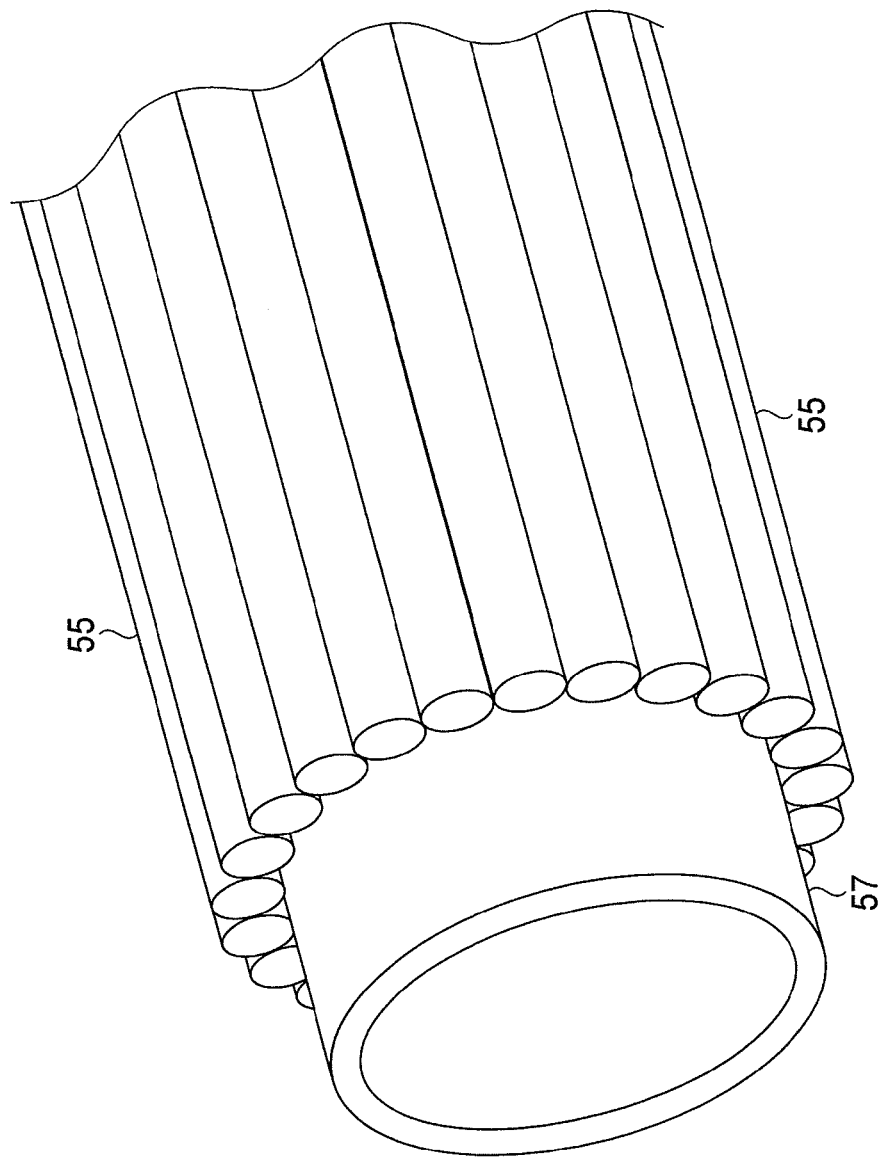
FIG. 10 is a perspective view of the image fibers and the hollow tube, which has been provided for the purpose of illustrating the arrangement of the image fibers on the hollow tube.

As shown in FIGS. 4 and 10, a plurality of the image fibers 55 is fixed around the hollow tube 57 so that the image fibers 55 surround the hollow tube 57. In addition, the image fibers 55 are fixed so that the axis directions of the image fibers 55 at the incident end and the hollow tube 57 are parallel.

Figure 11:
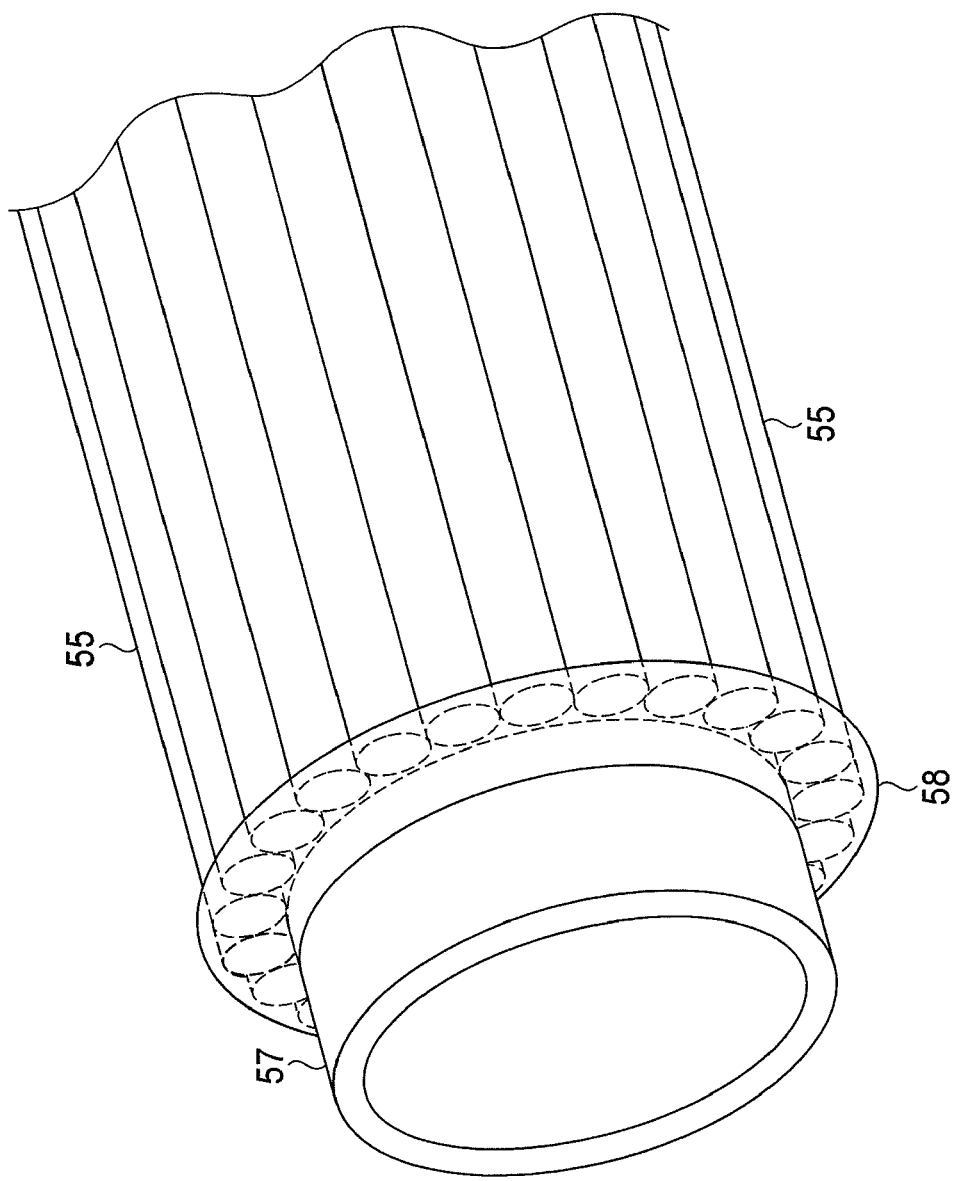
FIG. 11 is a perspective view of the image fibers, the hollow tube, and the ring lens, which has been provided for the purpose of illustrating the arrangement of the image fibers and the ring lens on the hollow tube.

As shown in FIGS. 4 and 11, the hollow tube 57 is inserted into a ring lens 58. The ring lens 58 is adhered to the incident ends of the image fibers 55.

Figure 12:
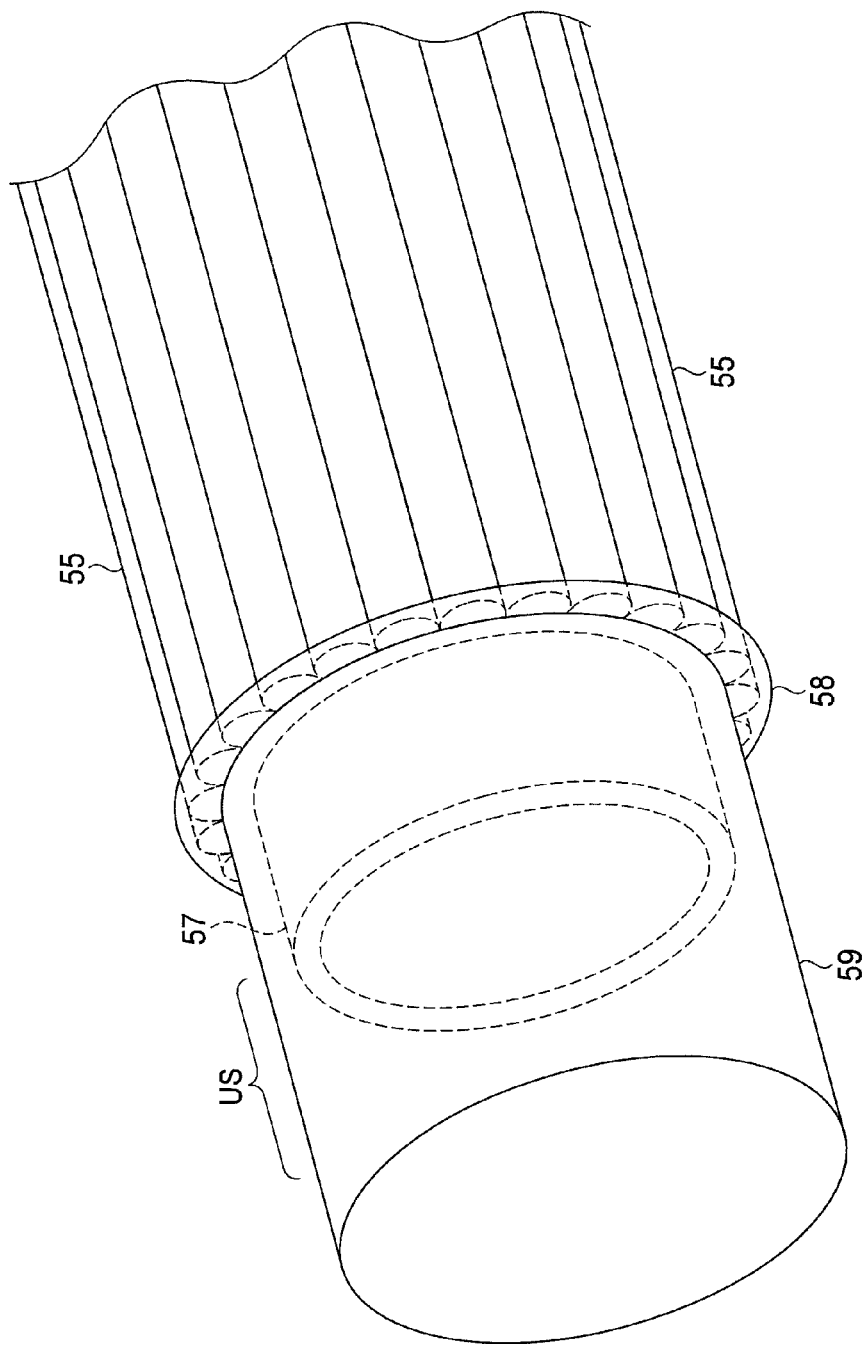
FIG. 12 is a perspective view of the image fibers, the hollow tube, the ring lens, and the tubular glass, which has been provided for the purpose of illustrating the arrangement of the image fibers, the ring lens, and the tubular glass on the hollow tube.

In addition, as shown in FIGS. 4 and 12, a head end of the hollow tube 57 is attached by insertion into the tubular glass 59. The hollow tube 57 is fixed without insertion through the tubular glass 59. The tubular glass 59 is colorless and transparent. Light passes from the inside of the tubular glass 59 at an uncovered section (see "US" in FIG. 4) that is not attached to the hollow tube 57.

Figure 13:
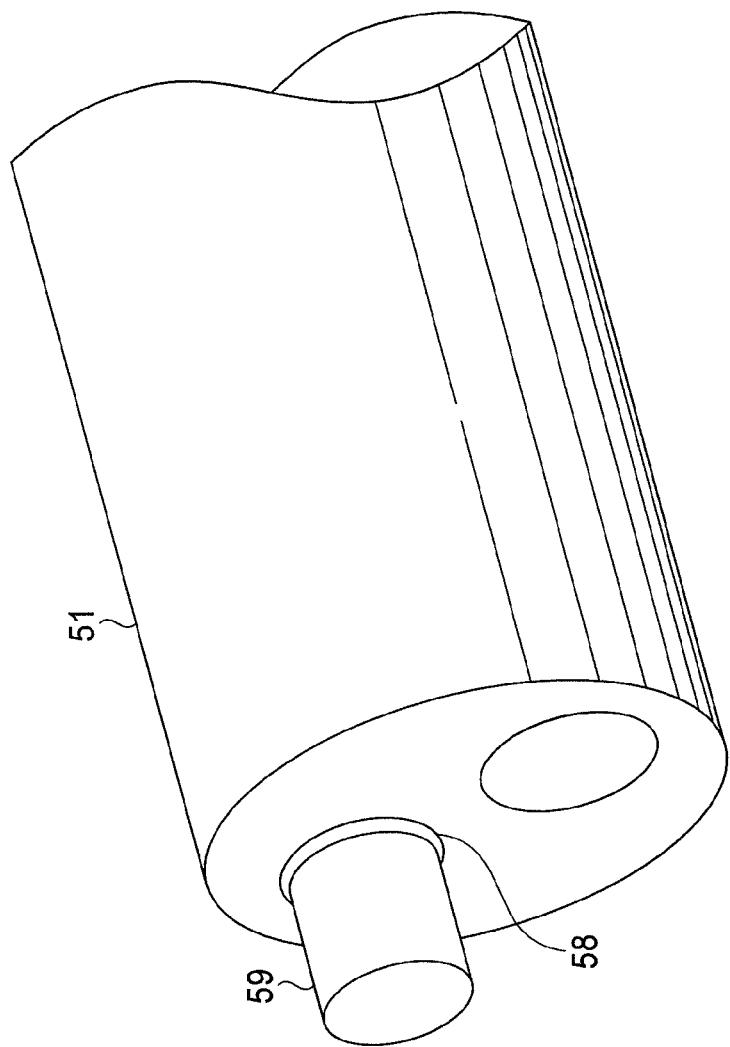
FIG. 13 is a perspective view of the distal end of the insertion tube.

As shown in FIG. 13, the image fibers 55, the hollow tube 57, the ring lens 58, and the tubular glass 59 are positioned so that the tubular glass 59 and the ring lens 58 protrude from the distal end of the insertion tube 51.

Figure 14:
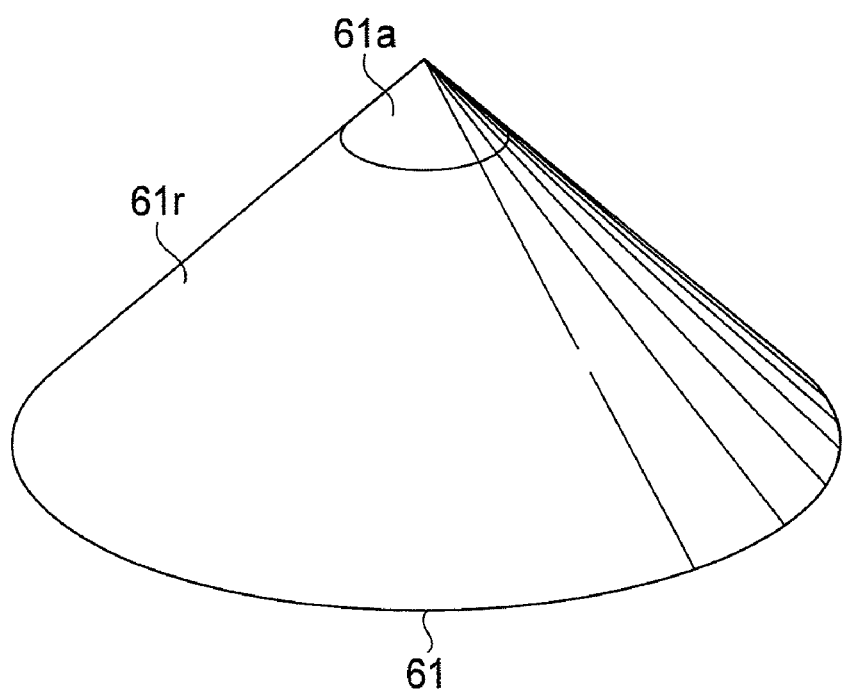
FIG. 14 is a perspective view of the mirror.

As shown in FIG. 4, a mirror fixing plate 60 is fixed onto an end of the tubular glass 59 opposite to the end attached to the hollow tube 57. On the mirror fixing plate 60 inside of the tubular glass 59, a mirror 61 is mounted. As shown in FIG. 14, the mirror 61 is shaped as a cone. On the outside surface of the mirror 61 is a reflection surface 61*r* that reflects the white laser beam emitted from the light-source unit 30. In addition, near the apex of the cone on the outside surface of the mirror 61 is also an attenuation surface 61*a* that attenuates the white laser beam.

The mirror 61 on the mirror fixing plate 60 is positioned so that the conical axis of the mirror 61 is aligned with a first straight line (see "L1" in FIG. 4) that passes the standard point and is parallel to the axis direction of the hollow tube 57. In addition, the mirror 61 is shaped so that the white laser beam, which is emitted from the emission end moved by bending and which is reflected by the reflection surface 61*r*, reaches the uncovered section (see "US") without reaching the hollow tube 57.

The end of the tubular glass 59 attached to the hollow tube 57 is entirely coated with a shielding film 59*f* (shield). The shielding film 59*f* prevents dissipated light, which leaks from the white laser beam before it can reach the observation area, from travelling along the tubular glass 59 and entering the incident ends of the image fibers 55 via the ring lens 58.

It is difficult to circulate or spirally move the emission end of the illumination fiber 53 in a stable manner within a circular area having a certain radius and the standard point as its center. A minimum radius that enables the emission end of the illumination fiber 53 to circulate in a stable manner is measured and defined as a first radius (first length).

Figure 15:
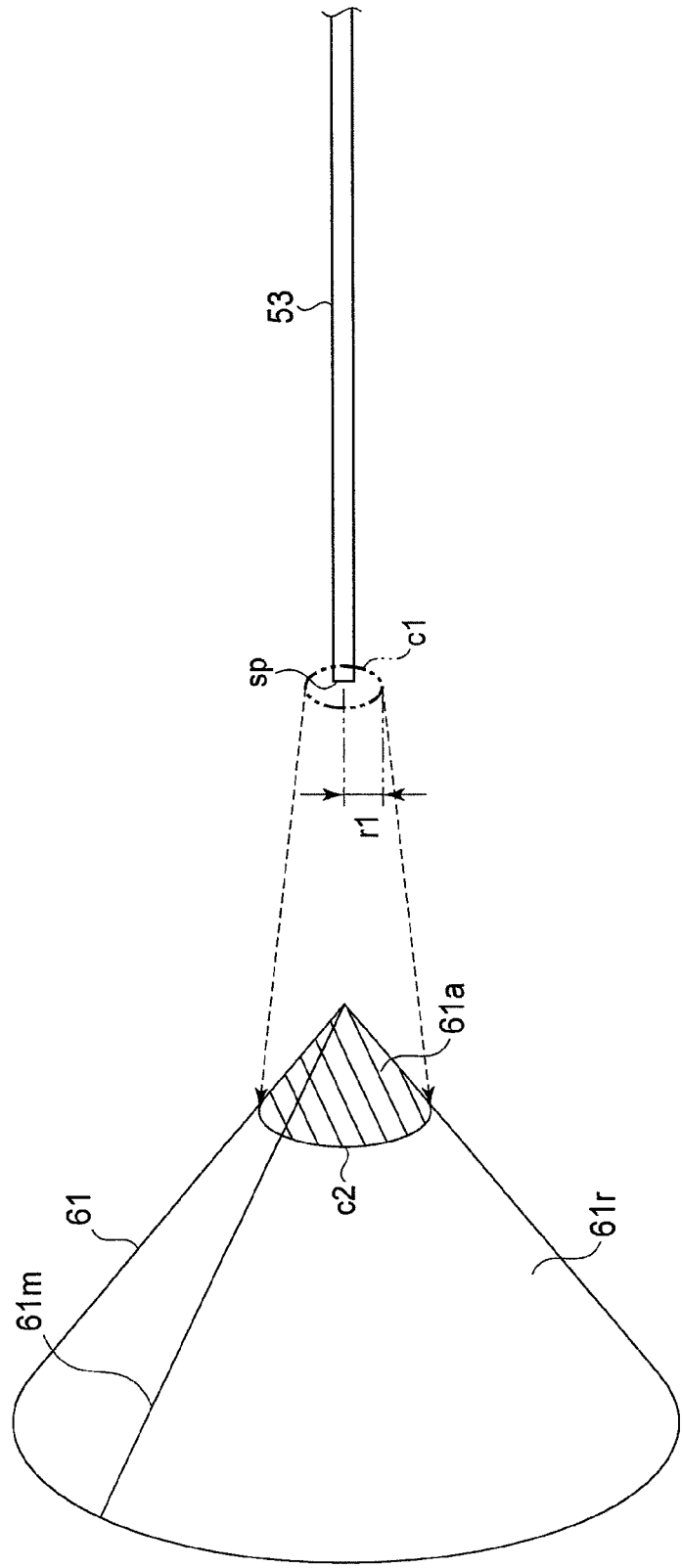
FIG. 15 illustrates the point on the mirror illuminated with the white laser beam when the emission end of the illumination fiber is moved along the first circumference.

As shown in FIG. 15, the white laser beam emitted from the emission end that is moved along a first circumference (see "c1") of a circular pattern with the standard point (see "sp") as its center and the first radius (see "r1") as its radius reaches a second circumference (see "c2") on the mirror 61. The second circumference is a locus defined by moving a point on the conical surface of the mirror 61 so that the distance from the moved point to the apex remains constant.

The attenuation surface 61*a* (see shaded area) is formed on the conical surface bounded by the apex and the second circumference. In addition, the reflection surface 61*r* is formed on the partial conical surface bounded by the second circumference and a circumference at the base of the conical mirror 61.

In addition, the reflection surface 61*r* has an initiation marker 61*m*, which is a line along the generatrix line of the conical mirror 61. The initiation marker is, for example, a black straight line, and absorbs the white laser beam incident on the initiation marker 61*m* without reflection.

Figure 16:
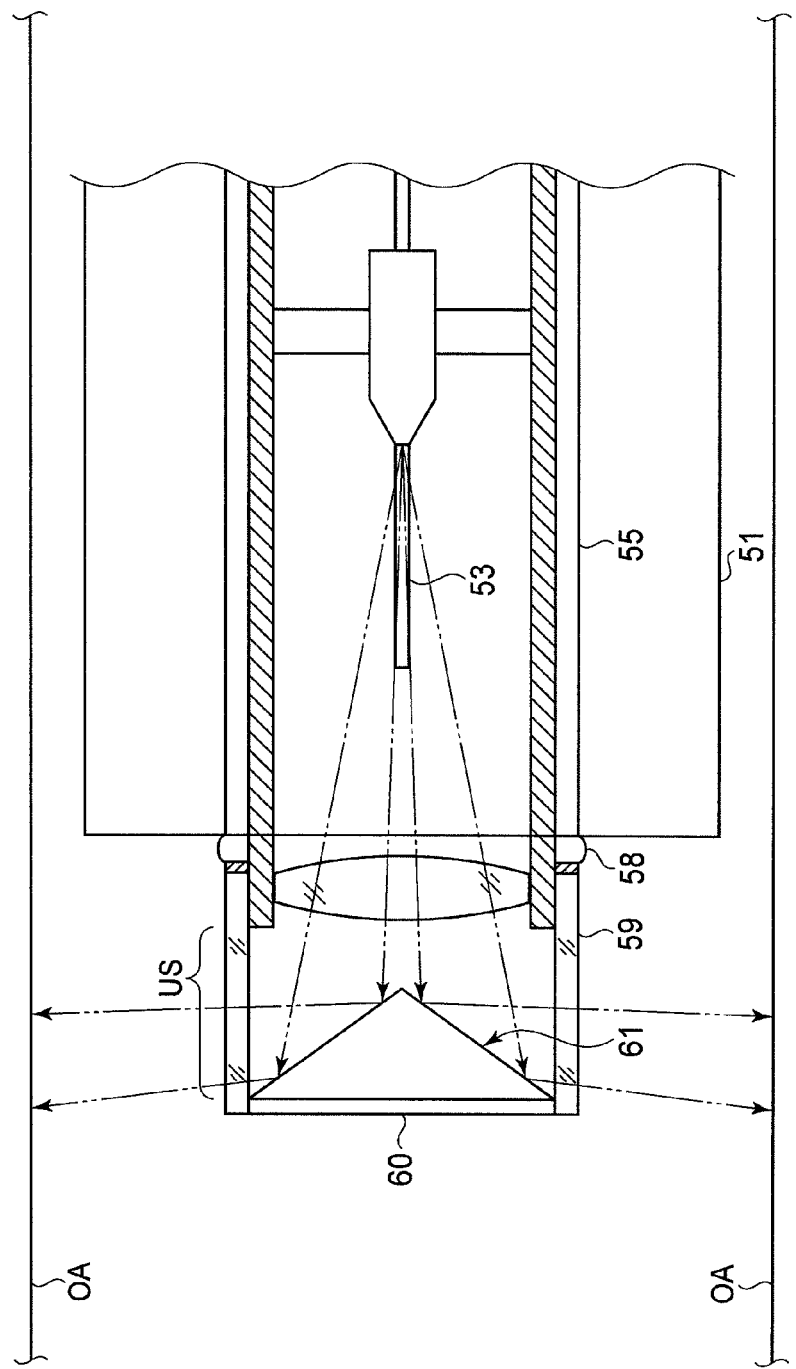
FIG. 16 illustrates a location illuminated with the white laser beam for scanning.

As shown in FIG. 16, the white laser beam emitted from the illumination fiber 53 is reflected by the mirror 61, passes through the uncovered section (see "US") of the tubular glass 59, and shined on the observation area around the tubular glass 59.

Figure 17:
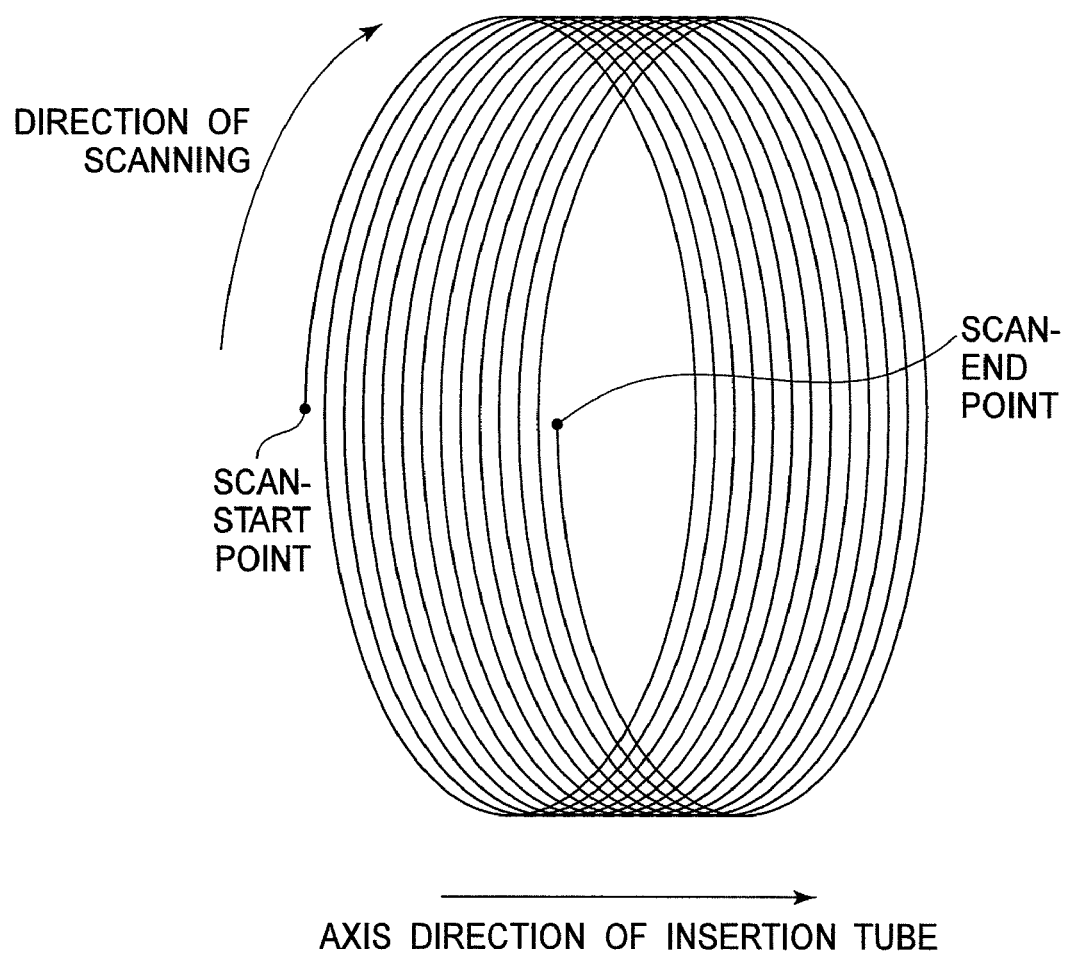
FIG. 17 illustrates a locus of the points of the observation area illuminated with the white laser beam emitted from the moving emission end of the illumination fiber.

As shown in FIG. 17, the point of the observation area illuminated with the white laser beam moves along a helical course. The observation area is scanned with the white laser beam by moving the illuminated point along the helical course. The point of the observation area, which is illuminated by the white laser beam when the white laser beam emitted from the emission end reaches the intersection point of the second circumference and the initiation marker 61m, is defined as the scan-start point. The point of the observation area, which is illuminated with the white laser beam when the emission end of the illumination fiber 53 is on the farthest point from the center of the spiral course, is defined as the scan-end point.

The reflected light is scattered at the point on the observation area that is illuminated with the white laser beam. The reflected light is condensed by the ring lens 58, and is made incident on the incident ends of the image fibers 55. The reflected light incident on the image fibers 55 is transmitted to the emission ends of the image fibers 55. As described above, the emission ends of the image fibers 55 are optically connected to the light-capturing unit 21. The reflected light transmitted to the emission ends is incident on the light-capturing unit 21.

The light-capturing unit 21 detects the amounts of red, green, and blue light components in the reflected light, and generates pixel signals according to the amounts of the light components. The pixel signals are transmitted to the image processing circuit 23.

The image processing circuit 23 estimates the points where the white laser beam is shined on the basis of signals used to control the scanner driver 22. In addition, the image processing circuit 23 stores the received pixel signals at the address of the image memory 26 that corresponds to the estimated points.

As described above, the observation area is scanned with the white laser beam, pixel signals are generated on the basis of the reflected light at the respective points illuminated with the white laser beam, and the generated pixel signals are stored at the address of the memory 26 corresponding to the points. The image signal corresponding to the observation area comprises the pixel signals corresponding to the points from the scan-start point to the scan-end point. As described above, the image processing circuit 23 carries out predetermined image processing on the image signal. After undergoing predetermined image processing, the image signal is transmitted to the monitor 11.

Figure 18:
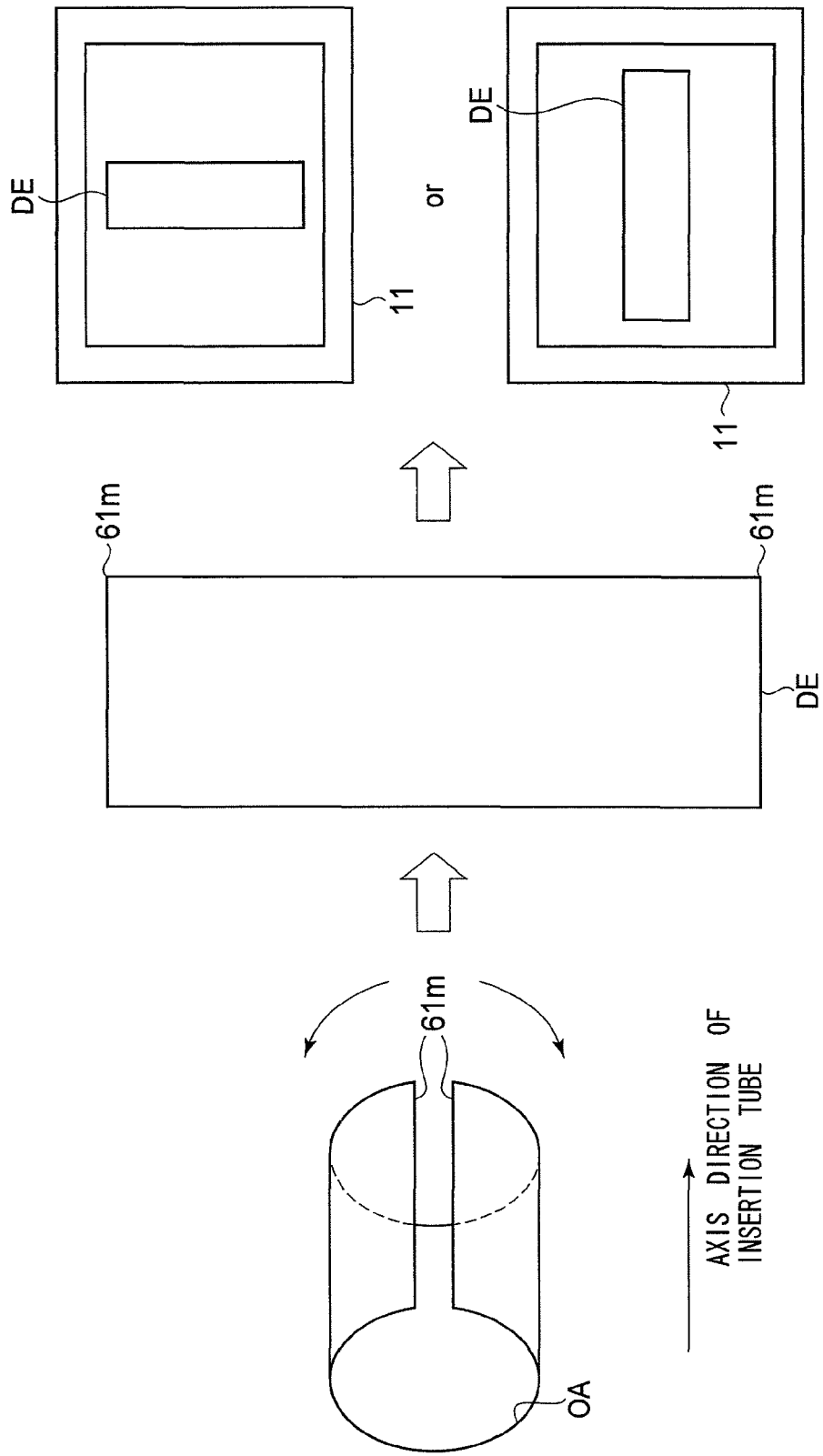
FIG. 18 illustrates the relationship between the form of the observation area scanned with the white laser beam and the development chart displayed on the monitor.

The development chart (see "DE" in FIG. 18) of the observation area (see "OA") scanned with the white laser beam along the helical course is displayed on the monitor 11. The development chart is a chart opened along the generatrix line, which corresponds to the initiation marker 61m, of the cylindrical image of the observation area.

In addition to the points where the white laser beam has been shined, the position of the emission end of the illumination fiber 53 is also estimated by the image processing circuit 23 on the basis of signals used to control the scanner driver 22. While the emission end of the illumination fiber 53 is moved along the first circumference, the emission of the white laser beam from the light-source unit 30, the generation of the pixel signals at the light-capturing unit 21, and the production of an image at the image processing circuit 23 are suspended.

To explain in detail, when the emission end of the illumination fiber 53 is moved within the first circumference, the system controller 25 controls the light-source unit 30 to suspend the emission of the white laser beam. On the other hand, when the emission end of the illumination fiber 53 is moved outside of the first circumference, the system controller 25 orders the light-source unit 30 to emit the white laser beam.

In addition, when the emission end of the illumination fiber 53 is moved within the first circumference, the system controller 25 controls the light-capturing unit 21 to suspend the generation of the pixel signals. On the other hand, when the emission end of the illumination fiber 53 is moved outside of the first circumference, the system controller 25 orders the light-capturing unit 21 to generate pixel signals.

In addition, when the emission end of the illumination fiber 53 is moved within the first circumference, the system controller 25 controls the image processing circuit 23 to suspend the production of an image. On the other hand, when the emission end of the illumination fiber 53 is moved out of the first circumference, the system controller 25 orders the image processing circuit 23 to produce an image.

Figure 19:
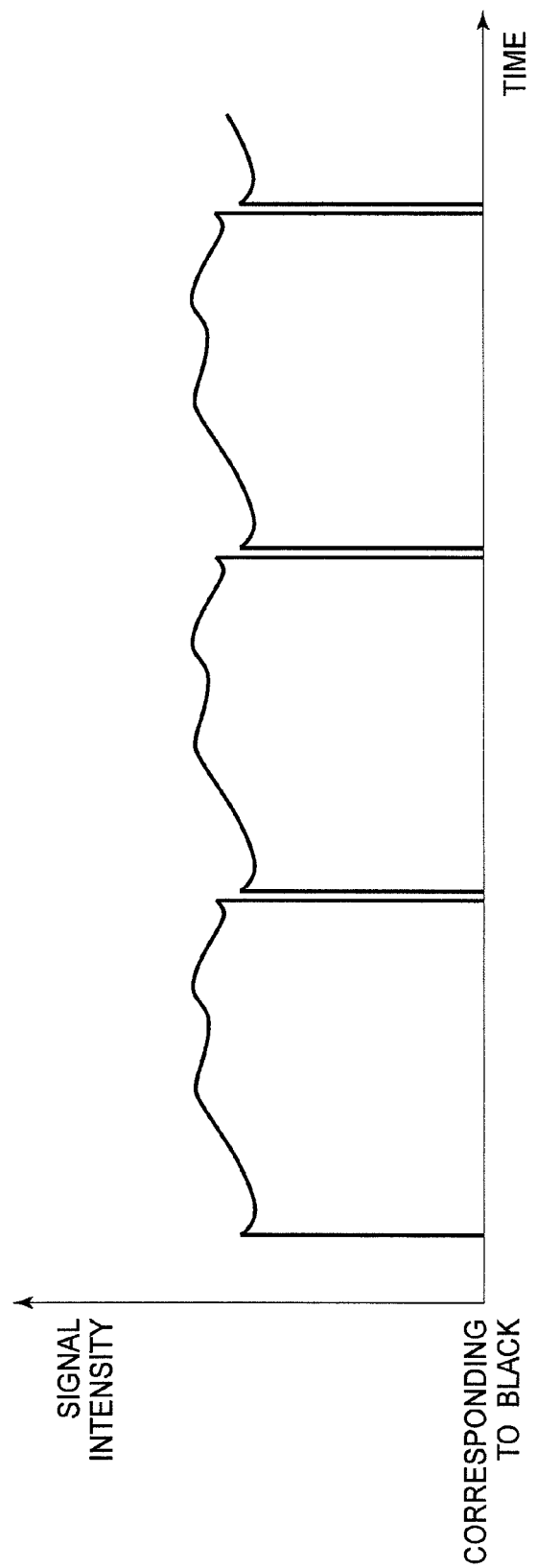
FIG. 19 is a graph illustrating the relationship between the signal intensity of the pixel signal and the elapsed time.

When the white laser beam emitted from the emission end of the illumination fiber 53 is incident on the initiation marker 61m, the white laser beam is not reflected by the mirror 61 and the white laser beam is not shined on the observation area. Accordingly, as shown in FIG. 19, the time when the signal intensity of the pixel signal is lowered to the signal intensity corresponding to black is determined to be the time when the point on the mirror 61, upon which the white laser beam from the emission end of the illumination fiber 53 is incident, is on the initiation marker 61m. On the basis of the signal intensity of the pixel signals, the image processing circuit 23 determines the time when the point upon which the white laser beam from the emission end of the illumination fiber 53 is incident, is on the initiation marker 61m. The time when the point upon which the white laser beam is incident is on the initiation marker 61m is used for estimating the position of the emission end of the illumination fiber 53.

In the above embodiment, a subject entirely around the insertion tube 51 is observable. Accordingly, a front view of an internal wall of a thin lumen is observable.

The mirror 61 is shaped as a cone, in the above embodiment. However, the shape of the mirror 61 is not limited to a cone. For example, a circular truncated cone with the reflection surface on a side can be used as the mirror. The shape of a bowl or a bell can be adopted. Other shapes can be adopted as long as the distance from the first position on the first straight line and any second position on the reflection surface increases with the distance between the first position and the illumination fiber 53. The line connecting the first and second positions is perpendicular to the first straight line. In other words, other shape can be adopted as long as the distance from the first position to any second position increases as the first position is moved toward the first direction.

The mirror 61 has the initiation marker 61m, in the above embodiment. However, the mirror 61 may not have the initiation marker 61m. It is possible to produce the development chart without using the initiation marker 61m by making an opening along the generatrix line of the captured image of the tubular observation area, which is a locus of the points illuminated with the white laser beam emitted from the illumination fiber 53, that is inclined toward a specified direction.

In addition, it is possible to estimate the position of the emission end of the illumination fiber 53 without the pixel signals corresponding to the initiation marker 61m. However, by estimating the position of the emission end using both the signals used to control the scanner driver and also the time when the point upon which the white laser beam is incident is on the initiation marker 61m, as in the above embodiment, the accuracy of the estimation can be improved.

The end of the tubular glass 59 is entirely coated with a shielding film 59f, in the above embodiment. However, the end of the tubular glass 59 does not need to be coated with the shielding film 59f. It is possible to capture only the reflected light from the observation area without the shielding film 59*f*. However, to produce a more accurate image it is preferable to prevent the white laser beam reflected by the mirror 61 from entering the incident end of the image fibers 55. Accordingly, it is preferable to coat the end of the tubular glass 59 with the shielding film 59*f*, as in the above embodiment.

The mirror 61 has the attenuation surface 61*a*, in the above embodiment. However, the mirror 61 may not have the attenuation surface 61*a*. Unless the mirror 61 has the attenuation surface 61*a*, the observation area is scanned with the white laser beam emitted from the emission end, which moves along the first circumference in an unstable manner.

However, it is still possible to produce an accurate image because the production of the image is suspended while the emission end is moved along the first circumference. Because of the attenuation surface 61*a* in the above embodiments, the white laser beam, which is unnecessary for illumination, is prevented from being shined on the observation area.

The emission end of the illumination fiber 53 is moved by inclining the illumination fiber 53, in the above embodiment. However, the emission end can be moved according to another method. The same effect as the above embodiment can be achieved by using another means to move the emission end of the illumination fiber 53 so that the point on the mirror 61 is illuminated with the white laser beam. In other words, the same effect as the above embodiment can be achieved by moving the emission end in the direction perpendicular to the emission direction of the white laser beam or any other direction including the direction perpendicular to the emission direction of the white laser beam from the emission end.

The emission end of the illumination fiber 53 is moved along the spiral course, in the above embodiment. However, the emission end can be moved along other courses.

The emission of the white laser beam from the light-source unit 30 is suspended when the emission end of the illumination fiber 53 is moved along the first circumference, in the above embodiment. However, the emission may not be suspended. As described above, it is possible to produce an accurate image even if the emission is not suspended, because the production of the image is suspended while the emission end is moved along the first circumference. Owing to the suspension of the emission as in the above embodiment, the power consumption can be reduced.

The generation of the pixel signals by the light-capturing unit 21 is suspended when the emission end of the illumination fiber 53 is moved along the first circumference, in the above embodiment. However, the generation may not be suspended. As described above, even if the pixel signals are generated when the emission end is moved along the first circumference, the pixel signals are not used for the production of the image signal because the production of the image is suspended while the emission end is moved along the first circumference. Accordingly, it is possible to produce an accurate image even if the generation is not suspended. Owing to the suspension of the generation of the pixel signals as in the above embodiment, the power consumption can be reduced.

The white laser beam is emitted from the light-source unit 30 as in the above embodiment. The light-source unit 30 may emit other kinds of light, such as excitation light that excites an organ to fluoresce. Then, autofluorescence incident on the incident end of the image fibers 55 can be transmitted to the light-capturing unit 21, and the image can be produced on the basis of the autofluorescence.

Although the embodiments of the present invention have been described herein with reference to the accompanying drawings, obviously many modifications and changes may be made by those skilled in this art without departing from the scope of the invention.

The present disclosure relates to subject matter contained in Japanese Patent Application No. 2008-296159 (filed on Nov. 19, 2008), which is expressly incorporated herein, by reference, in its entirety.

The invention claimed is:

1. A scanning endoscope system comprising a scanning endoscope and a scanning endoscope processor, the system comprising:

the scanning endoscope comprises:
a first transmitter that receives radiant light from a light source of the scanning endoscope processor and emits a beam of radiant light from an emission end, the beam of the radiant light being incident on an observation area;
an actuator that moves the emission end in a direction perpendicular to an emission direction, the beam of the radiant light being emitted from the emission end of the first transmitter in the emission direction;
a mirror is arranged at the emission end in the emission direction when the emission end is on a predetermined standard point, the mirror comprising a reflection surface around a first straight line, the first straight line being parallel to a first direction and including the standard point, the first direction being the emission direction of the radiant light when the emission end is on the standard point, a distance between a first position on the first straight line and any second position on the reflection surface increasing as the first position is moved in the first direction, the reflection surface reflecting the radiant light emitted from the first transmitter toward the observation area around the first straight line, a line connecting the first and second positions being perpendicular to the first straight line, an attenuation surface being provided on the mirror, the attenuation surface attenuating the radiant light emitted from the emission end when the emission end is within a first area, the center of the first area being the standard point, the radius of the first area being a first length;
the actuator moving the emission end along a spiral course with a center on the standard point; and
the scanning endoscope processor comprises:
a light source that supplies the radiant light to the first transmitter of the scanning endoscope;
a light receiver that receives and detects an amount of the reflected light or the fluorescence at the observation area illuminated with the radiant light;
an image processor that produces an image corresponding to the observation area on the basis of the amount of the reflected light or the fluorescence detected by the light receiver; and
a first controller that suspends the production of an image at the image processor when the emission end is within the first area, the first controller ordering the image processor to produce the image when the emission end is outside of the first area.

2. A scanning endoscope system according to claim 1, the scanning endoscope processor further comprising a second controller that suspends the emission of the radiant light from the light source when the emission end is within the first area, the second controller commanding the light source to emit the radiant light when the emission end is outside of the first area.

3. A scanning endoscope system according to claim 1, the scanning endoscope processor further comprising a third controller that suspends the detection of the amount of the reflected light or the fluorescence by the light receiver when the emission end is within the first area, the third controller commanding the light receiver to detect the amount of the reflected light or the fluorescence when the emission end is outside of the first area.

4. A scanning endoscope apparatus including a scanning endoscope and a scanning endoscope processor:

the scanning endoscope comprises:

a first transmitter that receives radiant light from a light source of the scanning endoscope processor and emits a beam of radiant light from an emission end, the beam of the radiant light being incident on an observation area;

an actuator that moves the emission end in a direction perpendicular to an emission direction, the beam of the radiant light being emitted from the emission end of the first transmitter in the emission direction;

a mirror is arranged at the emission end in the emission direction when the emission end is on a predetermined standard point, the mirror comprising a reflection surface around a first straight line, the first straight line being parallel to a first direction and including the standard point, the first direction being the emission direction of the radiant light when the emission end is on the standard point, a distance between a first position on the first straight line and any second position on the reflection surface increasing as the first position is moved in the first direction, the reflection surface reflecting the radiant light emitted from the first transmitter toward the observation area around the first straight line, a line connecting the first and second positions being perpendicular to the first straight line;

wherein the reflection surface is parallel to a side surface of a circular truncated cone, the first straight line being the axis of the circular truncated cone;

the actuator moving the emission end along a spiral course with a center on the standard point; and a light source that supplies the radiant processor light to the first transmitter of the scanning endoscope;

a light receiver that receives and detects an amount of the reflected light or the fluorescence at the observation area illuminated with the radiant light;

an image processor that produces an image corresponding to the observation area on the basis of the amount of the reflected light or the fluorescence detected by the light receiver; and a first controller that suspends the production of an image at the image processor when the emission end is within the first area, the first controller ordering the image processor to produce the image when the emission end is outside of the first area.

* * * * *